United States Patent [19]
Faccioli et al.

[11] Patent Number: 5,766,179
[45] Date of Patent: Jun. 16, 1998

[54] MECHANICAL SYSTEM FOR BLIND NAIL-HOLE ALIGNMENT OF BONE SCREWS

[75] Inventors: Giovanni Faccioli, Monzambano; Stefano Rossi, Verona, both of Italy

[73] Assignee: Orthofix S.r.l., Bussolengo, Italy

[21] Appl. No.: 812,363

[22] Filed: Mar. 5, 1997

[51] Int. Cl.⁶ .................................................. A61B 17/56
[52] U.S. Cl. .................................................. 606/98; 606/96
[58] Field of Search .................................. 606/98, 97, 96, 606/86, 87, 89, 62, 63, 64, 80

[56] References Cited

U.S. PATENT DOCUMENTS

| | | | |
|---|---|---|---|
| 5,352,228 | 10/1994 | Kummer et al. | 606/64 |
| 5,433,720 | 7/1995 | Faccioli et al. | 606/87 |
| 5,620,449 | 4/1997 | Faccioli et al. | 606/98 |
| 5,665,086 | 9/1997 | Itoman et al. | 606/64 |
| 5,681,318 | 10/1997 | Pennig et al. | 606/98 |

*Primary Examiner*—Guy V. Tucker
*Attorney, Agent, or Firm*—Hopgood, Calimafde, Kalil and Judlowe

[57] ABSTRACT

An all-mechanical system for bone-drilling alignment of a blind distal bone-screw hole of an installed intramedullary nail, wherein the system provides (i) a drill jig that features a longitudinally adjustable nail-contactable contact-rod mounting in the jig and (ii) a drill-guide which can align with the blind distal bone-screw hole for a correct nail-contactable adjustment of the contact rod. The system enables the surgeon to check-out the drill jig in assembled relation to a selected intramedullary nail, prior to nail installation, and to perform an adjustment to compensate for nail diameter when the contact end of the rod engages the nail. He can then either visually satisfy himself of the drill-guide/bolt-hole alignment, or he can use a plug-gage or trocar tool having guidance in the drill guide, and checking for whether the plug gage has entry into the bone-screw hole in the intramedullary nail. Having thus ascertained that the adjusted contact-rod position can correctly identify drill-guide alignment with one or more bone-screw holes of the intramedullary nail, it is only necessary, after installing the nail and connecting the jig to the proximal end of the nail, to make a small local surgical incision through flesh and bone sufficient to enable direct stabilizing (contact-rod) contact with the nail, whereupon it is known that the drill guides are in correctly drillable alignment with the targeted bone-screw holes of the installed nail. Drilling and setting of bone screws can immediately proceed in customary manner.

6 Claims, 7 Drawing Sheets

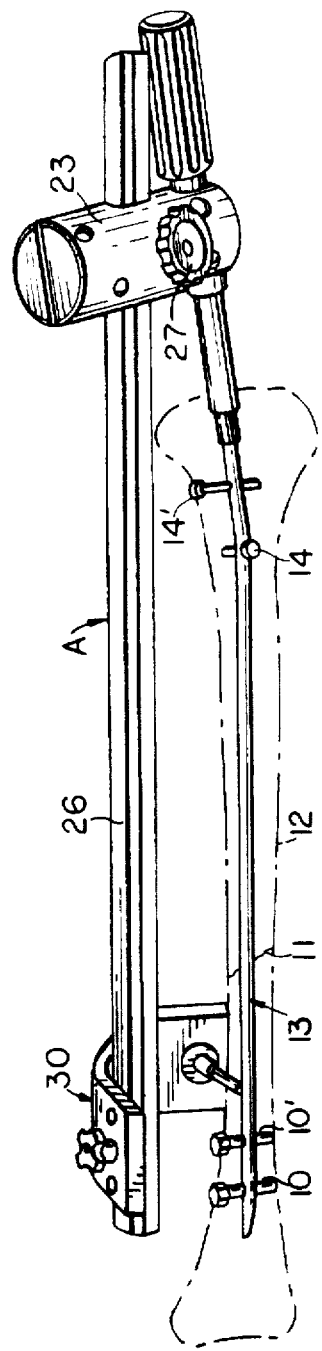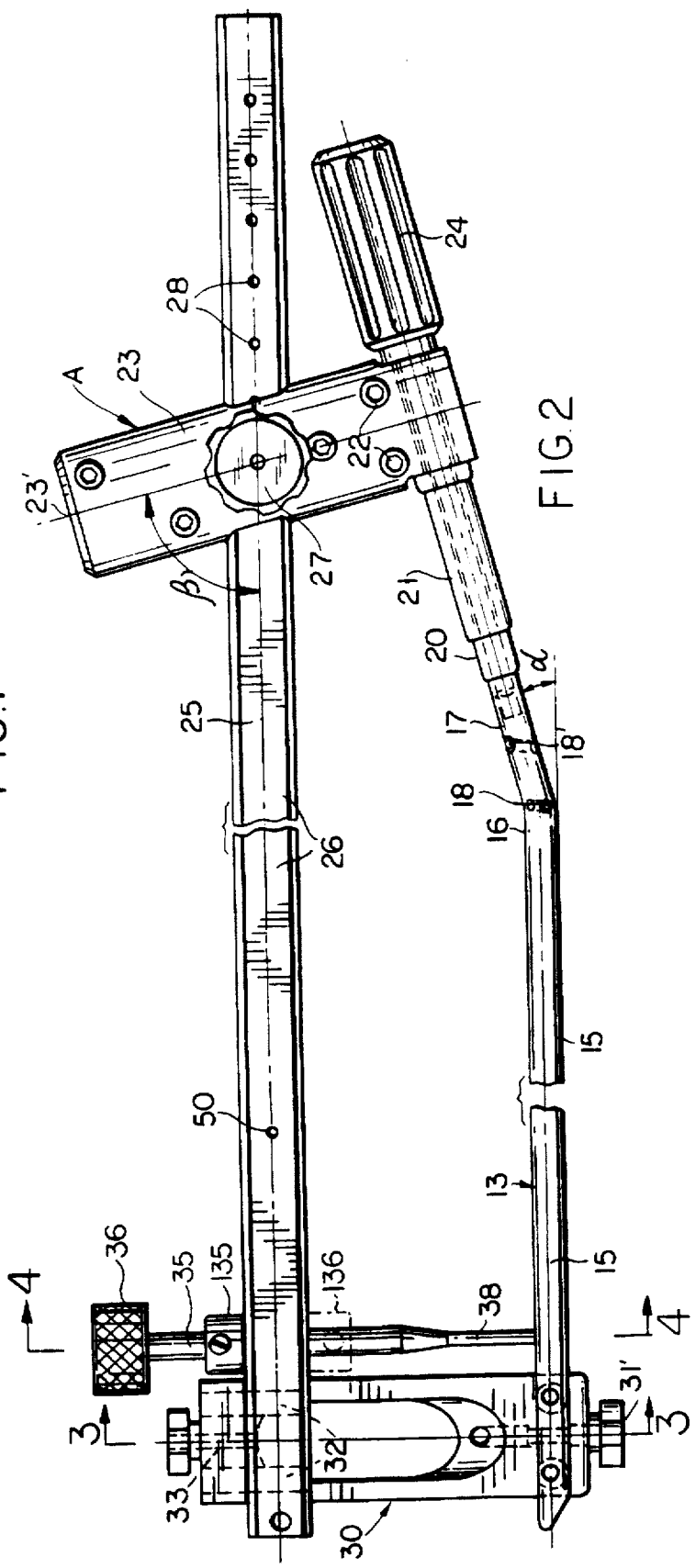

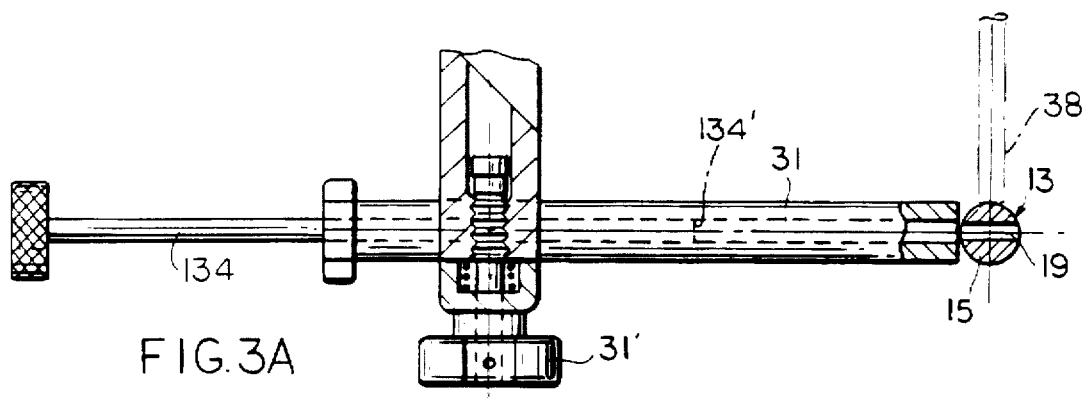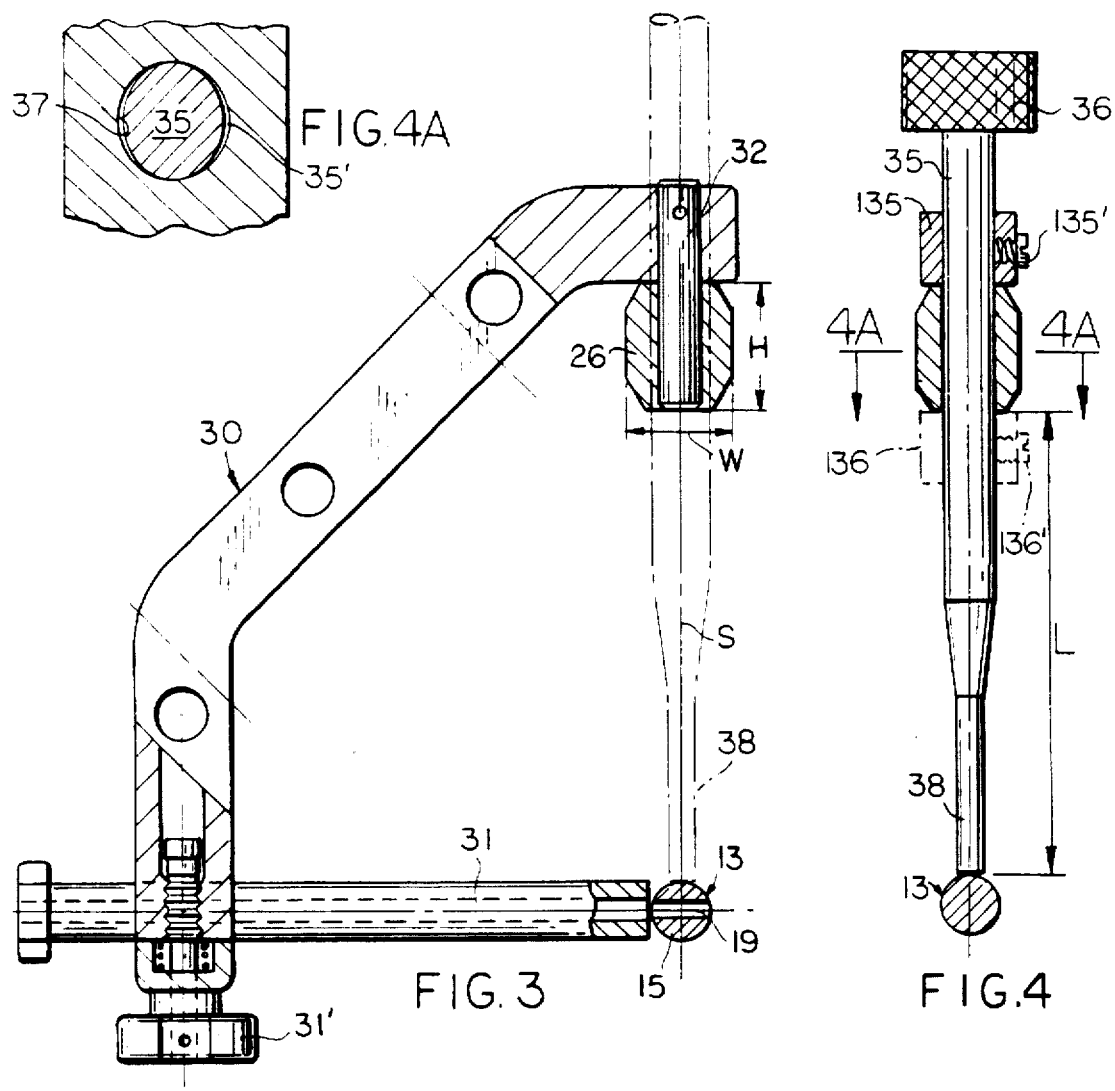

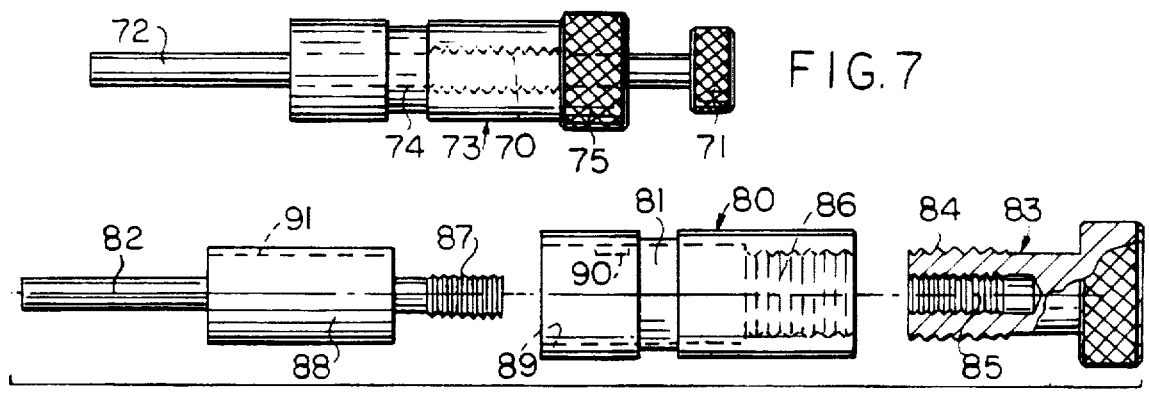
FIG. 7
FIG. 8
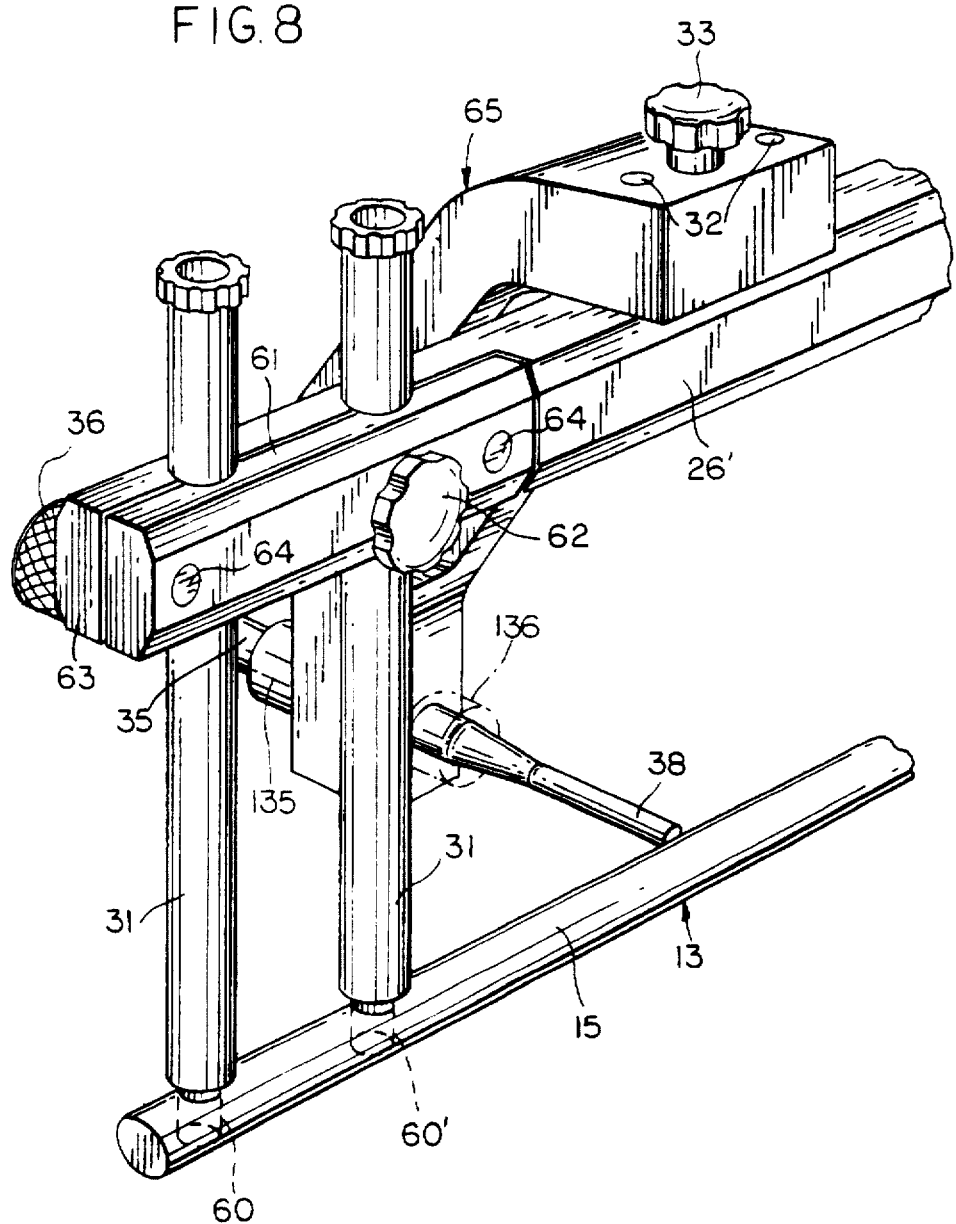
FIG. 6

MECHANICAL SYSTEM FOR BLIND NAIL-HOLE ALIGNMENT OF BONE SCREWS

BACKGROUND OF THE INVENTION

The invention relates to a jig system adapted for connection to an intramedullary nail, wherein the intramedullary nail is implanted in a fractured bone, such as a tibia or a femur, the implantation being such as to have the nail extend distally and proximally with respect to the fracture, in reinforcement of fractured parts of the bone that have been re-aligned or merely are to be held in alignment for the course of healing repair.

Intramedullary nails of the character indicated are either solid or hollow, but they are customarily prepared with two spaced parallel holes that extend diametrically across the nail near the distal end of the nail and with two spaced holes of similar nature, but not necessarily parallel, near the proximal end of the nail. These holes are formed to accept bone screws, and when the nail has been installed, its bone-screw holes are said to be "blind" in terms of the bone-drilling alignment that must be achieved. The problem has always been one of assuring correct alignment for drilling to accept a bone screw driven through bone for anchoring passage through the intramedullary nail. The traditional technique for assuring blind drill alignment with the bone-screw holes of an intramedullary nail involves use of x-rays, which of course pose well-known dangers from cumulative exposure; and to assure adequate safety for operating personnel, the use of x-rays is, to say the least, cumbersome, thus contributing to the expense of a good intramedullary-nail installation.

The proximal end of the nail is formed for anti-rotational keyed and detachably fixed connection to jig structure that is intended to aid in orientation of drill guides in the hope of achieving a correct alignment with each drill hole, the customary technique of ascertaining alignment being by use of x-rays.

One of the problems of locating a bone-screw hole in an installed intramedullary nail is the practical fact that the nail may have undergone a slight bend in the course of implantation, so that such holes at the distal end of the nail no-longer have precisely the same location with respect to the proximal end, as was the case prior to nail implantation. Thus, any jig structure connected to the proximal end has had to rely on x-rays for assurance of alignment.

In an effort to avoid x-ray dependence in solving the problem of locating blind bone-screw holes in an installed intramedullary nail, U.S. Pat. No. 5,281,224 and pending U.S. application Ser. No. 08/121,762 have proposed magnetic detection, in the scanning displacement of a detection system across the distal region of an installed nail, to locate the central axis of the nail; but in the present state of development, such techniques have been clinically awkward, achieving less than the accuracy that is required.

Also in an effort to avoid x-ray dependence in solving the problem of locating blind bone-screw holes in an installed intramedullary nail, pending U.S. application Ser. No. 08/401,094, filed Mar. 8, 1995, addresses the problem by purely mechanical techniques which involve a drill jig adapted for connection to the proximal end of the particular intramedullary nail selected for implantation in a patient's fractured bone; the distal end of the intramedullary nail has a customary pair of longitudinally spaced bone-screw or bolt holes, the axes of which locally intersect the longitudinal axis of the intramedullary nail. The drill jig is configured to position two geometric axes in generally quadrature relation to each other and respectively generally perpendicular to the longitudinal axis of the nail; one of these two axes is longitudinally positioned for alignment with at least one of the distal bolt holes of the intramedullary nail, while the other of these two axes is in nearby longitudinal offset from said one of the two axes. A contact rod is positionable by the guide on said other of these two axes, with special provision by way of a selectable shim, whereby it can be known that when the contact end of the rod is in contact with the selected intramedullary nail, the said one of these two axes is truly aligned (and is therefore adapted for true drill-guide alignment) with at least one of the bone-screw holes of the selected intramedullary nail. It should be noted that the selected shim for contact-rod positioning is designed to truly compensate for the local radius of the intramedullary nail, so that when contacted by the contact rod, the intramedullary nail will have automatically positioned at least one of its bone-screw holes in true alignment with a drill-guide axis.

While much can be said for the jig system of said pending U.S. application, it might be subject to criticism by the surgeon who is equipped for operation on different patients who he determines to require intramedullary nails of different diameter, e.g., as between the young and the adult of the surgeon's patients.

BRIEF STATEMENT OF THE INVENTION

It is an object of the invention to provide an improved all-mechanical jig system of the character indicated.

It is a specific object to meet the above object with a system which avoids the need for shims or their equivalent and which nevertheless is able to serve for assurance of bone-hole-aligned drilling of bone, regardless of the radius of a selected intramedullary nail.

It is another specific object to provide a jig of the character indicated, wherein adjustable means is provided in the jig structure for contact-rod positioning in the longitudinal axis of the contact rod.

Another specific object is to provide a simplified method of using an all-mechanical jig of the character indicated, wherein the surgeon can readily adjust the jig, prior to intramedullary nail implantation, for correct bone-screw hole alignment of a bone-drill guide, such that after intramedullary nail implantation, the jig can be relied upon to have correctly provided the axis for drilling the bone in alignment with the desired bone-screw hole.

The invention meets the above objects by providing an all-mechanical drill-jig system which features a longitudinally adjustable contact-rod mounting in the jig. The system enables the surgeon to check-out the drill jig in assembled relation to a selected intramedullary nail, prior to nail installation, and to perform an adjustment to compensate for nail diameter when the contact end of the rod engages the nail. He can then either visually satisfy himself of the drill-guide/bolt-hole alignment, or he can use a plug-gage or trocar tool having guidance in the drill guide, and checking for whether the plug gage has entry into the bone-screw hole in the intramedullary nail. Having thus ascertained that the adjusted contact-rod position can correctly identify drill-guide alignment with one or more bone-screw holes of the intramedullary nail, it is only necessary, after installing the nail and connecting the jig to the proximal end of the nail, to make a small local surgical incision through flesh and bone sufficient to enable direct stabilizing (contact-rod) contact with the nail, whereupon it is known that the drill guides are in correctly drillable alignment with the targeted bone-screw holes of the installed nail. Drilling and setting of bone screws can immediately proceed in customary manner.

BRIEF DESCRIPTION OF THE DRAWINGS

The invention will be described in detail for preferred embodiments having particular application to a tibial fracture, the description being in conjunction with the accompanying drawings, in which:

FIG. 1 is a simplified perspective view from above and to one side of an intramedullary nail and connected drill-jig structure of the invention, showing distal and proximal nails that have been installed in a fractured tibia, the tibia being shown in phantom outline, and flesh profiles being omitted in the drawing;

FIG. 2 is an enlarged view in side elevation of the jig and nail of FIG. 1, partly broken-away to provide greater detail of distal and proximal coaction between nail and jig components;

FIG. 3 is a further enlarged section of distal outrigger structure of FIG. 2, taken at 3—3 of FIG. 2;

FIG. 3A is a fragmentary view of a portion of FIG. 3, to illustrate a method of use of the drill-jig of the invention;

FIG. 4 is another view, to the scale of FIG. 3 and in partial section taken at 4—4 of FIG. 2 to show contact-rod stabilizer structure of FIG. 2;

FIG. 4A is a greatly enlarged fragmentary section taken at 4A—4A of FIG. 4, to show detail of a contact-rod adjustability feature;

FIG. 6 is a perspective view of drill-jig features of the structure of FIG. 5;

FIG. 7 is a view in elevation for contact-rod adjustment mechanism which is a modification of the adjustment mechanism of FIGS. 4 and 4A;

FIG. 8 is an exploded view of coacting elements of a differential-screw adjustment mechanism, being a modification from FIG. 7;

DETAILED DESCRIPTION

Figure 5:
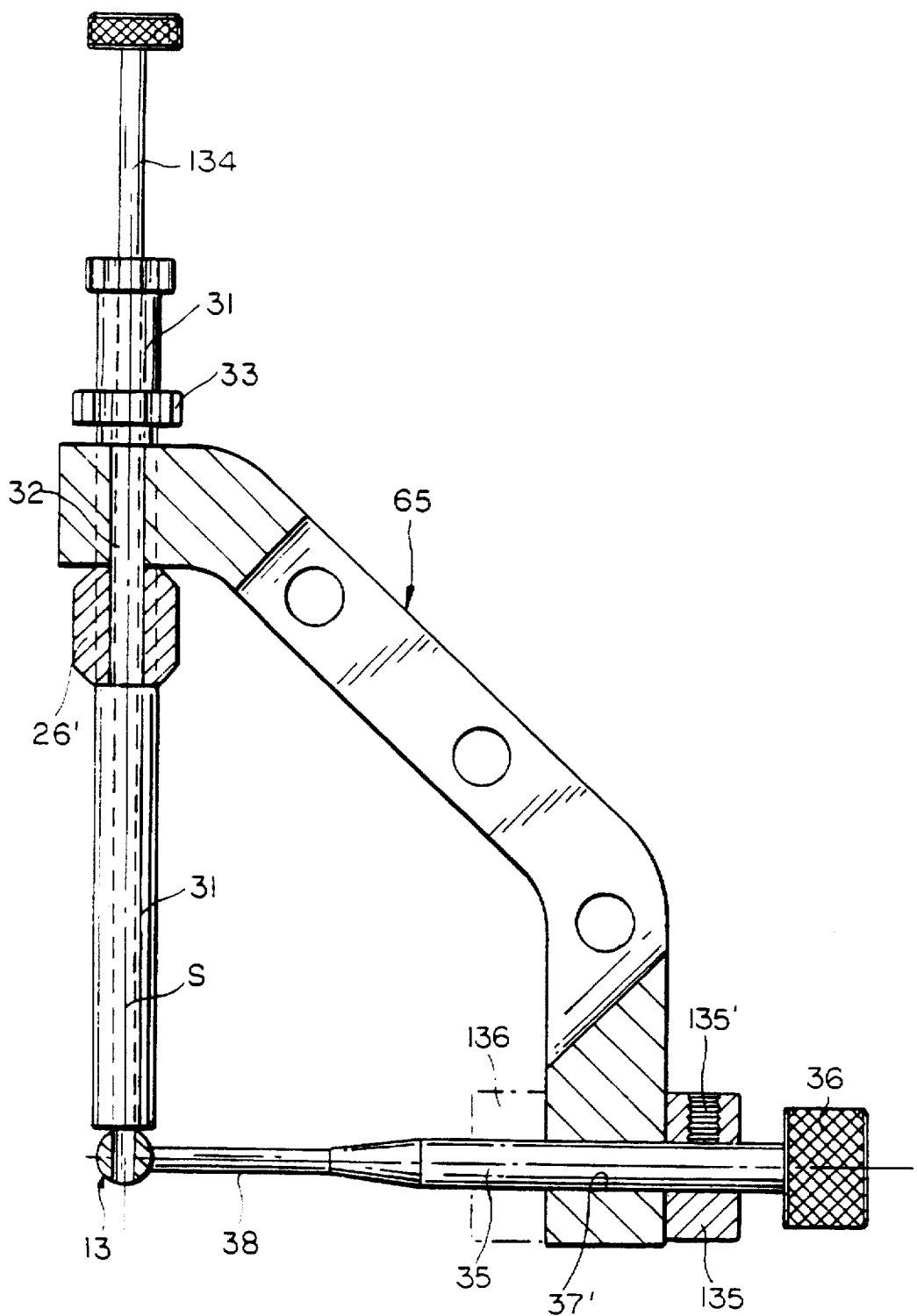
FIG. 5 is a view in side elevation corresponding to the view of FIG. 3, to illustrate a modification of the drill-jig of FIG. 2.

In FIG. 1, the invention is seen as jig structure, generally designated A, after having completed its job of correctly aligning, drilling and enabling installation of two bone screws 10, 10' at a location distal to a fracture 11 in a tibia 12 which has been reinforced by an elongate intramedullary nail 13; the bone screws 10, 10' will be understood to pass through spaced parallel bone-screw holes extending diametrically through nail 13. Two further bone screws 14, 14' are shown installed near the proximal end of the nail; the drilling for accommodation of bone screws 14, 14' is accomplished pursuant to description, in connection with FIGS. 9 and 10 of said copending U.S. application; such description and the same FIGS. 9 and 10 have been incorporated herein, for completeness.

Figure 9:
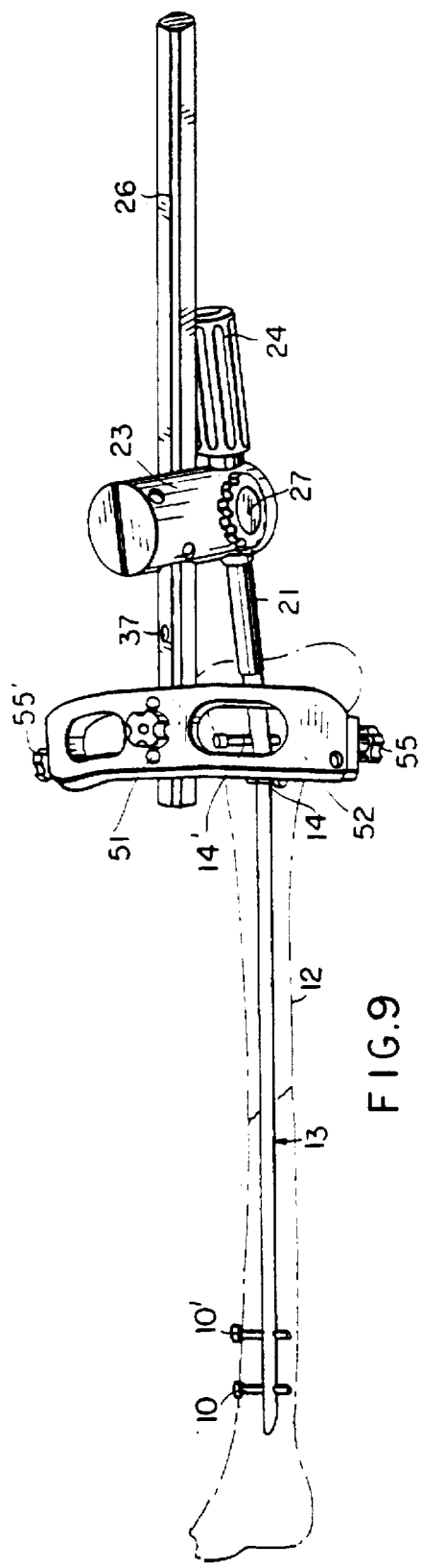
FIG. 9 is a view similar to FIG. 1, for the same jig but different outrigger structure, used to install two longitudinally spaced bone screws at mutually divergent orientations through bone, at the proximal end of the intramedullary nail of FIG. 2.
Figure 10:
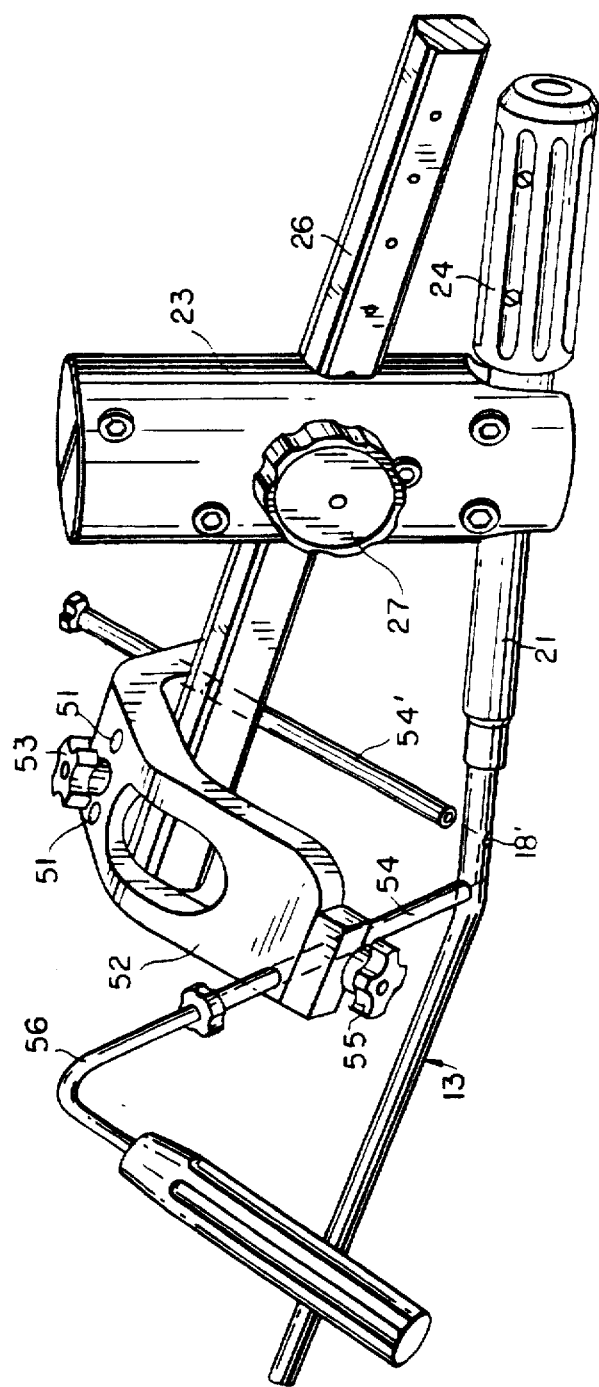
FIG. 10 is an enlarged view in perspective to show greater detail of outrigger, drill-guide and jig structure at the proximal end of the system.

The jig structure A comprises a plurality of separably and adjustably connectable components, better seen and identified in FIG. 2, where the intramedullary nail 13 is shown to comprise an elongate straight distally extending portion 15 for most of its length, there being a short bend 16 at an acute angle a near the proximal end 17 of the nail; two spaced diametrically extending bone-screw holes 18, 18' in the bent proximal end 17 are for accommodation of the screws 14, 14' to be described later in connection with FIGS. 9 and 10. The bend 16 between otherwise straight distal (15) and proximal (17) portions of nail 13 will be understood to define a single plane of symmetry which will be referred to as the sagittal plane, containing the bent axis of the nail; and the distal bone-screw holes (as at 19 in FIG. 3) for bone screws 10, 10' will be understood to be normal to the sagittal plane.

The proximal end of nail 13 has keyed fit to jig A via the chuck 20 of an elongate locking rod 21, which is clamped by bolts 22 between front and back halves of a handle 23. A knob 24 is rotatable to releasably secure the engagement of jig structure in accurately keyed and longitudinally located relation to the proximal end of the nail. As thus clamped and engaged to the nail, the central axis 23' of handle 23 extends at a right angle to the axis of the proximal end 17 of the nail, and this central axis 23' lies in the sagittal plane of the connected nail.

Confronting faces of the bolted halves of handle 23 are grooved to establish a central axis 25 for slant-guided alignment of an elongate guide bar 26, wherein the central axis 25 of bar 26 intersects the central axis 23' of handle 23 and wherein axis 25 is also contained within the same sagittal plane of the nail; the slant angle β of intersection of axes 23, 25 is the complement of angle α, so that guide bar 26 is necessarily parallel to the elongate distal end portion 15 of the intramedullary nail. The cross-sections of guide bar 26 and of the handle grooving to accommodate bar 26 are non-circular and preferably rectangular, with a height dimension H which exceeds its width dimension W, suitably by about 25 percent, as seen in FIG. 3, wherein corners of the section are bevelled. A locking knob 27 carried by handle 23 includes a dowel portion which is selectively enterable in a given one out of a plurality of spaced transverse openings 28 in bar 26, the selection among openings 28 being dependent upon the length of the particular intramedullary nail 13 selected for implantation. It is preferred that openings 28 be of limited depth in bar 26 and that the bottom of each opening 28 be conical, so that with a conically-tipped dowel secured by locking knob 27, the cone-to-cone engagement will assure an accurate, play-free location of handle 23. In an alternative employment, to be later discussed in connection with FIG. 11, the knob 27 will be understood to be a schematic indication of selectively operable clamping means which does not necessarily require use of spaced openings, the knob 27 serving for selective clamping of handle 23 to bar 26' of FIG. 11, whatever the selected length, as will become clear.

Distal outrigger structure 30 is removably carried by guide bar 26 near the distal end of bar 26, to provide such lateral and downward offset of its lower end, from bar 26 and away from the sagittal plane, as to enable precise spaced parallel orientation and clamping of two elongate drill guides 31, in alignment with each of the respective bone-screw holes 19 near the distal end of the nail 13, all as best seen in FIG. 3; a knob 31' enables clamped positioning of the drill guides 31 to the laterally offset end of outrigger 30. For accuracy in establishing the indicated offset, the upper end of outrigger 30 mounts two spaced dowels 32 having precision entry in vertical guide bores through guide bar 26, and outrigger 30 is securely clamped by a knob-driven locking bolt 33 engaged to a suitably tapped vertical bore in guide bar 26, located between the two dowel pins. The vertical orientation of dowel pins 32 and of the guide bar 26 symmetrically with respect to the sagittal plane S of nail 13 is clear from FIG. 3 and its legends. Thus, the mounting of the outrigger is reversible, depending upon the leg to be operated upon; and in the case of operations to be performed on a fractured tibia, it will be understood that the outrigger 30 will have been mounted to bar 26 on the medial side of the tibia.

A further important component of the jig of FIG. 2 is an elongate spacer or stabilizer "contact" rod 35, having in the form shown, a manipulating knob 36 at its upper end. For most of its length, rod 35 may be of constant diameter for guided stability in a vertical bore 37 in guide bar 26, in spaced adjacency to the mounting of outrigger 30; however, as seen with some exaggeration in FIG. 4A, the section of vertical bore 37 and the section of rod 35 may each be slightly elliptical such that diametrically opposed maximum crescents 35' of clearance exist for a tightened or locked knob rotation of rod 35 with respect to the vertical bore, and such as to enable free longitudinal positioning of rod 35 when rod 35 is rotated to relieve the locking engagement. For a purpose which will later become clear, a collar 135, guided on rod 35, is releasably securable by set-screw means 135' to retain an adjusted stop position of rod (35) extension beyond bar 26, the same being suggested by the designation L in FIG. 4; it will be understood that when the twist-lock mechanism of engagement 35/37 is released, rod 35 and its locked (adjusted) stop collar 135 are bodily removable out of reception and guidance in bore 37. Optionally, as suggested by phantom outline in FIG. 4, another collar 136 (also with set screw, not shown in FIG. 4) may be selectively locked to rod 35 and in engagement to the underside of bar 26 (when collar 135 has been positioned and locked to rod 35), thereby positively locating an adjusted longitudinal positioning of rod 35.

At its lower end, the diameter of rod 35 is reduced to define a cylindrical portion 38 which, as will later be explained, must be passed through a small surgical incision of flesh and a local drilling of bone, to permit lower-end contact, as shown, with nail 13.

It will be helpful briefly to outline steps taken with the described jig A to assure quick and accurate drilling of bone for distal bone-screw anchorage to an installed intramedullary nail 13. First, an intramedullary nail 13 should be selected for nail diameter and overall length to serve the surgeon's purposes, in the light of a particular fracture 11. Suitable surgery is performed to assure entry of the selected nail in direct alignment with the medullary cavity, but first it is recommended that, at least for distal-drilling purposes, the selected nail be assembled to the jig A to ascertain correct length adjustment (via dowel knob 27) at the correct one of the predrilled locations 28 along guide bar 26. Outrigger 30 should be assembled to bar 26, along with two drill guides 31, securely setting the knob of bolt 33 and of the drill-guide clamp 31'. Additionally, stabilizer contact rod 35 should be inserted in bore 37 in guide bar 26, with the collar set screw 135' backed off so that collar 135 is freely slidable on rod 35. Visual sighting for drill-guide bore alignment with bone-screw holes may be sufficient, but it is preferred to use a plug-gage or trocar 134 (see FIG. 3A) inserted for guidance in a drill-guide bore and into locating engagement in the applicable one of the bone-screw holes 10—10' of the intramedullary nail, thus positively aligning the bore and the hole on a simple alignment axis 19. At this point, rod 35 should be run up to abutment of its end 38 with the surface of the intramedullary nail, and collar 135 should be clamped by set screw 135' in abutment with bar 26, as shown in FIG. 4, before set-screw clamping to rod 35, to retain collar 135 as a reference stop which reflects the adjustment. The plug gage or trocar 134 may then be removed, as may also the stabilizer rod 35, with its clamped reference stop provided by collar 135. The bar 26 and its handle 23 may also be removed, as a unit, from chucked assembly to the intramedullary nail, so as to allow the surgeon to surgically implant the intramedullary nail before reestablishing chucked assembly to the drill jig at handle 23. All is now in readiness to prepare for a correctly aligned drilling procedure.

After installing nail 13, whether the nail be solid or hollow, with the handle 23 of the jig (A) remaining locked in its keyed connection to the proximal end of the nail, the guide bar 26 will be understood to have been locked at its pre-established point for locking-screw retention via knob 27 at one of the length-section bores 28 in guide bar 26; for convenience, the upper surface of the guide bar 26 will be understood to have been inscribed with unit-length markers at unit spacing, corresponding to the length of intramedullary nails of an available set, and it will be further understood that engraved length designations, such as 280, 300 . . . in increments of 20-mm up to 400-mm, may be inscribed adjacent successive length markers, as the same may have been available from which to have selected nail 13. Such numerical inscriptions alongside successive length markers that are readable, as at bar-26 emergence from guidance through handle 23, will be understood to have enabled the surgeon to have made fast and correct length adjustment and locking of bar 26, in support of the distal operations to be performed, and in the context of having already made the precision adjustment of the length L.

As already noted, the distal outrigger 30 will have been initially mounted on guide bar 26 so that it is positioned on the medial side of the tibia, and the drill guides 31 should be backed off into the outrigger to determined proper locations for the incisions. An incision is then made beneath each screw guide, and the medial cortex is exposed in each incision by blunt dissection, taking care to avoid entrapment of or damage to the saphenous nerve and vein. The guides 31 are then advanced until they are in contact with the medial cortex. The clamp 31' on outrigger 30 is then tightened to hold the screw guides firmly in place.

Before any bone-screw holes are drilled, the system must be stabilized in position for exact drilling alignment with the bone-screw holes 19 of the nail. To this end, a drill guide (not shown) is inserted into the vertical bore 37 which has been previously described for stabilizer-rod (35) accommodation; an incision is made in the skin directly beneath this vertically oriented drill guide, and the anterior tibial cortex is exposed by blunt dissection. The drill guide is then advanced until its teeth are engaged onto the anterior border of the tibia; whereupon, a drill bit (e.g., of 4-mm diameter) is used to drill only the anterior cortex, and the drill bit is then removed. At this stage, because of the shape of the drill bit, the hole in the bone is tapered, so that a square-ended 4-mm T-handled reamer (not shown) can be passed down to the nail, and intervening debris is removed. The hand reamer and vertical drill guide are now removed and are replaced by entry of stabilizer rod 35 in vertical bore 37, the same being inserted to the point of reduced end (38) passage through the drilled hole in the cortex and into contact with nail 13. The stabilizing rod 35 must be set in the correct position for the particular diameter of nail 13, by making sure that the adjusted collar 135 abuts bar 26; and to positively lock rod 35 in its correct position, the optional second collar 136 should abut the underside of bar 26, as above-described.

In similar fashion, the drill guides 31 are positioned close enough to locate the zones of flesh to be surgically invaded until the anterior tibial cortex is exposed by blunt dissection, and the drill guides are sufficiently advanced into close clearance with the tibial cortex, for guidance of the desired drilling operation. The outrigger 30, its screw guides engaged to the bone, and its stabilizer rod 35 engaged to the nail, now have the relationship shown in FIG. 3, except that drill guides 31 are backed off from nail 13 because bone section is yet to be drilled to create a bolt-accepting alignment with the bolt hole 19.

An assistant to the surgeon may now find it necessary to press on the knob 36 of the stabilizer rod, with stop collar 135 in abutment with bar 26, thus pressing its lower end or tip into loaded contact with the nail 13, in which case it is well that the second collar 136 has been added to clamp the correctly adjusted position of contact rod 35. This procedural step will be seen to achieve the following:

1. The surgeon is assured that the distance between the nail and the guide bar is precisely what it was checked out to be prior to nail insertion in the medullary canal, and this fact also allows for take-up of any bending of the nail in the sagittal plane, thus maintaining and assuring alignment of the distal drill-guide (31) targeting of bone-screw holes 19 in the nail; and
2. The guide bar 26 and outrigger 30 are stabilized, so that the surgeon has a secure platform for drilling distal holes in the bone.

Those skilled in the art of setting bone screws through correctly drilled "blind" distal holes in bone should not need further instruction, but it is perhaps well to review successive steps that are recommended for drilling and distal locking, as follows:

(i) The surgeon's assistant should maintain constant gentle downward pressure on the knob 36 of stabilizer contact rod 35, throughout the procedure which follows, as far as step (x) below.

(ii) A 4-mm drill guide is inserted into one of the guides 31, and is gently tapped to engage its distal-end teeth in the medial cortex.

(iii) A drill stop is locked to a selected 4-mm drill bit at the proximal end.

(iv) The drill bit is inserted into the drill guide, down to the bone, with the drill bit chucked to a hand-held electric drill, before the drill is started.

(v) The surgeon now drills steadily through the medial cortex, and stops the drill when the second cortex is reached.

(vi) The drill stop is moved proximally until it is 5-mm above the top of the drill guide, and is locked into place. This resetting of the stop represents an allowance for the thickness of the second cortex.

(vii) Drilling now continues through the second cortex. The drill stop prevents damage to tissues beyond the bone, and also provides a method of estimating the correct length of locking screw.

(viii) The drill bit is removed with the drill guide.

(ix) An angled trocar is selected and now inserted into the screw guide, so that it passes through the nail, and engages in the far cortex. The trocar has now stabilized the position of the guide bar and outrigger.

(x) Now that the screw-guide alignment is held by the trocar, the assistant may release the pressure on the T-handle of stabilizer contact rod 35.

(xi) The locking screw length, from the base of the screw head, is determined by measuring the amount of drill bit protruding from the drill guide.

(xii) The drill stop is now replaced at the proximal end of the drill bit, in readiness for repeating the drilling procedure for the other one of the distal bone-screw holes of nail 13.

(xiii) The second locking hole is now drilled, using exactly the same technique.

(xiv) The length of the second locking screw is determined as before.

(xv) A locking screw of correct length is now inserted into the second guide 31, and pushed through the bone, as with a suitably marked T-wrench, until the thread engages with the medial cortex. The locking screw is now turned clockwise, exerting gentle pressure, until a mark on the shaft of the T-wrench reaches the top of the screw guide. [It is important not to continue turning after this position is reached, otherwise the thread in the bone will be stripped.]

(xvi) The trocar is removed from the first guide 31, and the same technique is followed for the insertion of the second locking screw, after which both guides 31 are removed by loosening the guide-locking knob 31'.

(xvii) A check should now be carried out with an Image Intensifier or by x-ray to confirm that both screws have passed through the nail and to confirm that the reduction has been maintained.

(xviii) The distal outrigger 30 and the stabilizer or contact rod 35 are now removed.

Having completed first the distal installation of bone screws, and before proximal locking, the fracture should be examined by x-radiation to determine whether there is any remaining distraction. If there is, conventional techniques are known, whereby to reduce the distraction, so that proximal locking can proceed.

For proximal-locking use of the jig A, and with the distal outrigger 30 and stabilizer rod 35 removed, it is first necessary to reset guide bar 26 in handle 23, by setting the locking knob 27 so as to engage and lock handle 23 to bar 26 via another locating bore 50 near the distal end of bar 26. This will expose the two dowel-engageable bores at the distal end of bar 26, for acceptance of the two locating dowels 51 of a proximal outrigger structure 52. In the case depicted, the two bone-screw holes 18, 18' for proximal bone-screw anchorage are on orthogonally related axes that are longitudinally spaced from each other; the proximal outrigger 51 therefore straddles guide bar 26 via its central body region, with its dowel pins 51 projecting downward from its central body region, and with provision for locking the outrigger to the guide bar by way of knob-driven means 53. Drilling access on the respective axes of these holes 18, 18' is at equal and opposite 45° inclinations with respect to the sagittal plane of nail 13, and therefore the proximal outrigger 52 provides at one of its ends for clamped mounting of a drill guide 54 in alignment with hole 18, and, at the other of its ends, for clamped mounting of a second drill guide 54' in alignment with the other proximal bone-screw hole 18'. Clamping access for setting the drill guides 54, 54' is identified at knobs 55, 55' in FIGS. 9 and 10.

Procedurally, it is not necessary for the surgeon to check out his jig settings of drill guides prior to nail 13 implantation in the fractured bone, as long as the surgeon has become familiar enough to rely on proper use of correct accessories, such as the distal outrigger 30 and the proximal outrigger 52 for a given nail 13. However, before the surgeon has become that familiar with the jig and its proper use, it is well that he additionally check out the coordination of events and relationships at the proximal drilling alignments, as well as the distal drilling alignments, all prior to implantation of nail 13 in the tibia. FIG. 10 shows the relation of parts, for such checking at the proximal drilling sites, prior to nail 13 implantation. Not only does FIG. 10 show that each of the drill guides 54, 54' may be checked for accuracy of registration with the respective proximal bone-screw holes 18, 18', but FIG. 10 additionally shows use of a trocar 56 inserted in one (54) of the drill guides and into stabilizing entry of the aligned bone-screw hole 18 (not visible in FIG. 10, but shown in FIG. 2).

Use of the proximal-locking feature of the jig for proximal drilling is very much as for the case of distal drilling although there is no need for a stabilizer (nail-contact) rod 35 or its equivalent, since proximal drilling is so close to the location of jig connection.

After locking the pin or knob 27 to the proximal reference location 50 (see FIG. 2) on guide bar 26, the proximal outrigger 52 is mounted and locked to bar 26, and two screw guides 54 and 54' are clamped at 55, 55' to locate proper sites for the incisions. Two incisions are made, one antero-lateral and one antero-medial, and the tibial cortex is exposed in each case by blunt dissection. The screw guides 54, 54' are advanced down to the cortex and locked in position via clamp knobs 55, 55'. A drill guide is inserted into one of the screw guides, and tapped gently to engage its distal teeth into the cortex. The drill bit is pushed down to the bone, and pressed against the cortex before drilling begins. Further procedures track those described for distal locking. The bone screws are inserted after each hole is drilled, and their length is determined, as described for distal insertion of bone screws.

The modification of FIGS. 5 and 6 illustrates that the invention is also applicable to use of intramedullary nails wherein the axes of spaced parallel bone-screw holes 60, 60' for distal-end fixation to bone are in what may be called the sagittal plane, whether the nail is of bent or straight configuration, the point being that when the proximal end of the nail is keyed in its chucked connection to handle 23, the guide bar, here identified as 26', is parallel to the straight portion 15 of the intramedullary nail. The axes of the straight portion 15 of the nail, and the jig guide bar 26', and of the bone-screw holes 60, 60' are thus all in the sagittal plane, marked S in FIG. 5.

Since the drilling for bone-screw alignment with nail holes 60, 60' must now also be in the sagittal plane, the distal end of guide bar 26' is seen to provide for the releasably clamped mounting of drill guides 31 for such drilled alignment. Specifically, the distal end of bar 26' is so devised that a clamp block 61 may be clamped via knob actuation at 62 to support the precise spaced parallel relation of two drill guides 31. To this end, the confronting vertical faces of block 61 and of the uncut remainder 63 of the distal end of bar 26', are formed with matching cylindrically arcuate concavities for drill-guide support, and guide pins or dowels 64 carried by block 61 will be understood to have precision location and guidance in corresponding bores (not shown) in the distal-end portion 63 of bar 26'.

An outrigger 65 is generally as described for the outrigger 30 of the first embodiment, in that it has spaced parallel guide pins 32 and a locking knob 33 for accurate and secure outrigger mounting to the upper surface of guide bar 26'. However, the laterally and downwardly offset other end of the outrigger is devised for guidance and selective positioning of a spacer or stabilizer rod 35 in alignment with the central axis of the distal nail portion 15 and perpendicular to the sagittal plane. For this purpose, a stabilizing/contact rod 35 may be adjustably positioned in a bore 37' in the offset end of the outrigger, for nail-contacting assurance as described for rod 35 in FIG. 3, the difference being that in FIGS. 5 and 6, contact-rod stabilizing abutment with the nail must assure fidelity of drill-guide alignment with bone-screw holes 60, 60' pursuant to preliminary adjustment of collar 135 in FIGS. 5 and 6.

In use of the embodiment of FIGS. 5 and 6, the same procedures outlined above for distal-end use of the device of FIG. 2, will be seen to be equally applicable, except for the fact that spacer bar (35) and drill-guide (31) orientations are reversed in their respective references to the sagittal plane S.

Figure 11:
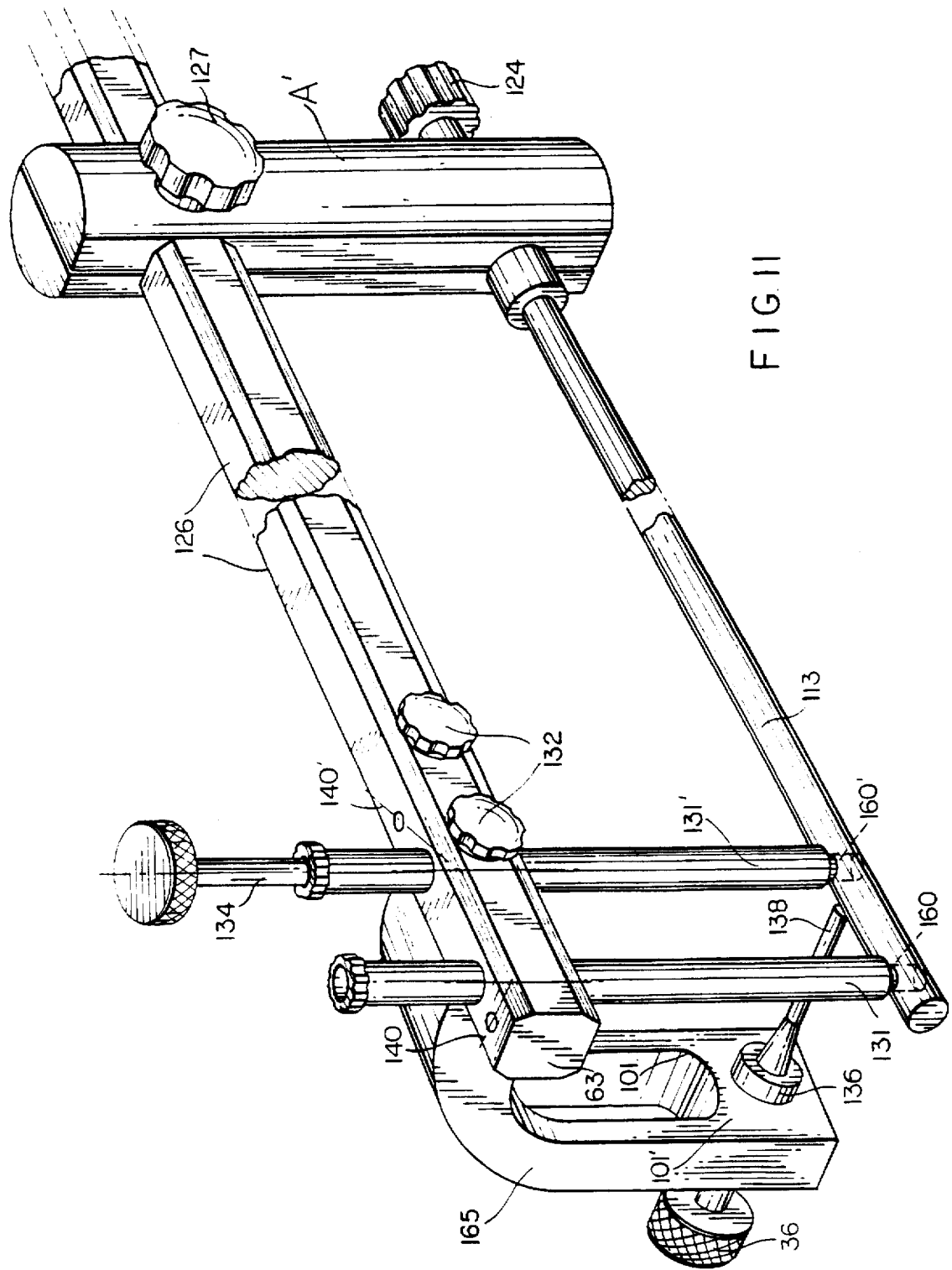
FIG. 11 is a simplified view in perspective, to illustrate a further alternative drill-jig construction.

The embodiment of FIG. 11 is in many respects similar to that of FIGS. 5 and 6, except that the embodiment of FIG. 11 is of specific utility in the blind-hole drilling of a fractured femur, wherein the intramedullary nail 113 is straight, with distal transverse bone-screw holes 160, 160' which are on parallel axes that are perpendicular to the central axis of nail 113 and thus determine a first geometric plane of symmetry. The handle A' has selectively locked and keyed connection to the proximal end of nail 113; handle A' extends perpendicular to nail 113 within the plane of symmetry, and handle A' is also perpendicular to elongate guide-bar structure 126, with means 127 whereby to selectively clamp structure 126 (i) in the indicated plane of symmetry and parallel to nail 113, and (ii) with such distally offsetting projection of structure 126 as to position its two drill guides 131/131', in potential (if not actual) aligning registration with the bone-screw holes 160, 160' of nail 113. Set screws on inclined axes 140/140', and accessible via the upper surface of jig bar 126, will be understood to provide adjusted axial positioning of drill guides 130/130', respectively.

The distal end of bar structure 126 is shown carrying the upper end of outrigger structure 165 which has a vertical-plane mounting face that is in clamped abutment with one of the vertical faces of the constant cross-section of guide-bar structure 126, being clamped by knob-headed bolts 132 which seat against the opposite vertical face of structure 126. It will be understood that bolts 132 have smooth cylindrical dowel-like fit to transverse bores in bar structure 126 and that only their threaded distal ends engage threaded bores in the confronting upper end of the outrigger structure 165. The lower (and laterally offset) end of outrigger structure 165 has a guide bore on an axis perpendicular to the axis of nail 113 and also perpendicular to the indicated first geometric plane of symmetry, for slidable guidance of a stabilizing rod 135; rod 135 will be understood to be equipped with locking collars, as at 135', to preserve an adjusted contact-rod (135) length, as described for collars 135, 136 in FIG. 5. Rod 135 has a manipulating knob 36 at its proximal end, and a reduced distal end 138 for stabilizing contact with nail 113.

In FIG. 11, the clamp bolts 132 are shown on spaced axes that symmetrically straddle the vertical axis of the drill guide 131', thus assuring that the reduced end 138 of the stabilizer rod will contact nail 113 in the geometric plane which is defined by the axis of nail hole 160' and the stabilizer-rod axis. This is a geometric plane of symmetry dividing the entire outrigger structure, perpendicular to the plane of symmetry defined by jig bar 126, nail 113 and the nail holes 160/160'. It will be understood that by thus providing the means to establish accurate drilling of bone on the axis of hole 160', the accurate drilling of bone on the axis of hole 160 is achievable without further set-up or manipulation, in view of the relatively close proximity of axes of holes 160/160' to each other. And it will be further understood that simple unthreading removal of bolts 132 will release the entire outrigger/stabilizer assembly for reversible application with respect to the opposite side of the geometric plane of jig bar 126 and the nail-hole axes to be accessed by drilling via drill guides 131/131'.

Thus far, the preliminary (i.e., pre-surgical) use of various embodiments of described drill jigs has illustratively relied upon different configurations for releasably setting the contact rod 35 and its nail-contacting end, in a precisely predetermined position for drill-guide (31) alignment with one or more bone-screw holes, particularly near the distal end of an intramedullary nail. The different combinations, already described to achieve this result, will now be itemized, along with further embodiments, as the same appear in FIGS. 7 and 8.

(1). An elliptical-section rod (35), in conjunction with an elliptical bore (37), as in FIG. 4A for selective relative rotation to lock or unlock a given longitudinal setting which has been found to be correct for bone-drilling alignment with one of the bone-screw holes of an intramedullary nail. Use of collar (135), set-screw retained to rod (35) provides a means of ready mechanical memory of the correct setting, while permitting temporary removal or back-off of the contact end 38, from nail-engaging contact. Once the nail has been installed in the patient, and the jig (A) has been reassembled to the proximal end of the nail, and a clean surgical access has been provided for contact-rod engagement to the installed nail, the collar (135)-fitted rod (35) may be reassembled to bar 26 or to outrigger 30, and a second collar 136 is advisedly provided in added assembly to rod, for secure retention of the predetermined adjustment.

(2). Use of a plug gage, trocar or the like to first align the drill guide of the jig with at least one of the bone-screw holes of the intramedullary nail;

(a) in conjunction with a rotary-locking configuration, as described in item (1) above and shown in FIG. 4A; or (b) in conjunction with rod 35 having a cylindrical shank and guided in a cylindrical bore, with selectively positionable stop collars, as described in item (1) above, and (c) use of either (a) or (b) above, in conjunction with a jig bar 26 which does not rely on selectively clamped handle (23) engagement to a preformed one or more fixed locating formations (28) on the bar 26, but which utilizes selectively operable clamp means (27) coacting between handle (23) and bar (26), in the context of plug gage, trocar or the like alignment of the drill-guide bore with the bone-screw hole (19, 60, 60') to longitudinally fixate the handle (23)-to-bar (26) engagement.

(3). Use of a removable contact-rod subassembly as in FIG. 7, wherein a single threaded engagement 70 is adjustable via a knob 71 to determine a precise longitudinal location of rod-end (72) contact with the intramedullary nail, the threaded engagement 70 involving external threads of rod 72, and internal threads in the bore of a sleeve 73 that is preassembled to rod 72. The sleeve 73 has a circumferential groove 74, providing spaced sidewalls which are to be understood as suggestive of means whereby sleeve 73 may be longitudinally retained in precise removably assembled relation to the contact-rod mounting bore, which is in the bar 26 or in the outer-end of the outrigger 30, depending upon the alignment orientation of the drill guide axis with a bone-screw hole of the intramedullary nail. Locking means to releasably secure a given rotary (i.e., longitudinal) adjustment of rod 72 to sleeve 73 is suggested at a locking rig 75, rotatably carried by the outwardly facing end of sleeve 73.

(4). Use of a removable contact-rod subassembly as in FIG. 8, wherein a mounting sleeve 80 is circumferentially grooved at 81, in the manner and for the purposes described above for sleeve 73 of FIG. 7. The embodiment of FIG. 8 incorporates a differential-screw mechanism to provide for finely divided longitudinal adjustment of the longitudinal position of nail contact by rod end 82, in response to selective rotary adjustment of a knob-end part 83. Part 83, the rod-end part 82, and sleeve 80 are the only parts and they are configured to provide the differential-screw relationship. Thus, the shank 84 of part 83 has external threads of first pitch and direction of thread advance; the bore 85 of shank 84 is internally threaded with a different pitch and opposite direction of thread advance; the external threads of shank 84 engage mating internal threads 86 at one end of sleeve 80; external threads 87 at the proximal end of the rod-end part 82 have mating engagement to the internal threads in the bore 85 of the knob-end part 83; and a cylindrical bearing portion 88 of rod-end part 82 has longitudinally guided support in a cylindrical bore 89 of sleeve 80, subject to antirotational engagement of a key 90 in bore 89, with a longitudinal key-engaging groove 91 at an angular location of the outer surface of bearing portion 88. The difference between thread advance in one direction at 85/87 on the one hand, and in the opposite direction at 84/86 will be understood to account for finely divided adjustment of the nail contacting end 82, for a given direction of rotary adjustment of the knob-end part 83, and this rotary adjustment can be provided with enough friction to retain the adjustment even though the subassembly of FIG. 8 is removed from engaged connection to the jig, via groove 81.

Figure 12:
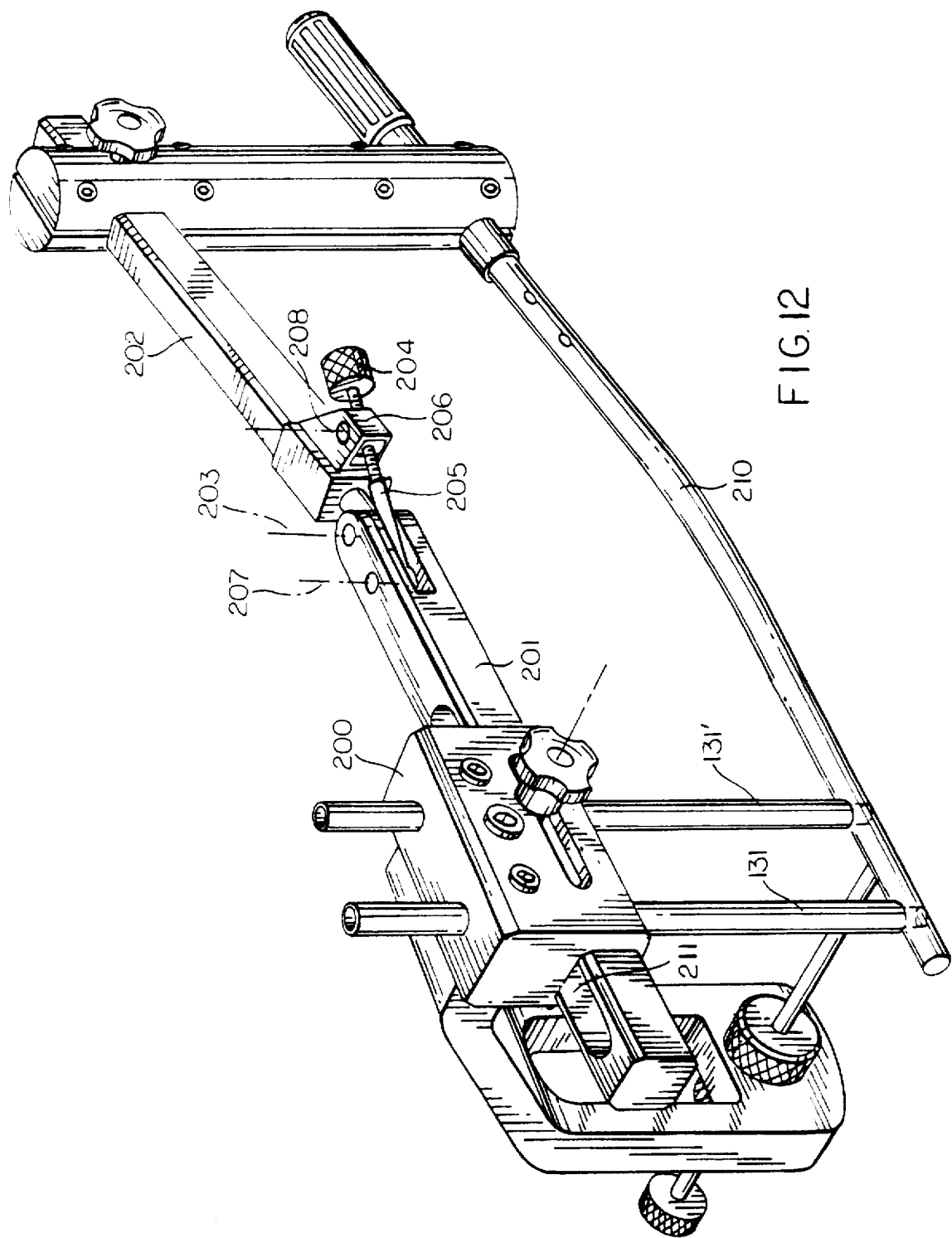
FIG. 12 is a still further perspective view, to illustrate another alternative drill-jig construction.

In FIG. 12, the spaced parallel drill guides 131, 131' are carried by a slide 200 which has a range of longitudinal adjustment along a distal-end portion of a distal supporting-bar element 201 having articulating connection to a proximal supporting-bar element 202, the axis of articulation being designated 203. Manually adjustable knob means 204 is available to drive a short threaded portion of a rod 205 which is pinned at its outer end to distal bar element 201 on a second connection axis 207, at longitudinal offset from articulation axis 203; threaded adjustment by knob 204 may be by way of a nut which is pivotally supported in a lateral bracket 206 of the proximal bar element 202, the axis of pivot action being designated 208. The purpose of the articulating connection is to enable the jig of FIG. 12 to adapt to the situation in which an intramedullary nail 210 having a central bend between straight proximal and distal ends can be accommodated, with positioning of spaced parallel distal bone-screw holes in accurate register with the respective axes of drill guides 131, 131'.

For the situation depicted in FIG. 12, a handle 209 is connected to the proximal bar 202, with selectively operable clamp means 214 to secure a given longitudinal location of bar-element clamping to handle 209. And chuck means 213 carried by the other end of the handle will be understood to have keyed orienting engagement to the proximal end of nail 210, such that the bend in the nail occurs in a horizontal plane (to which drill guides 131, 131' are perpendicular), and such that the longitudinal center of the bend of the axis of the nail is in substantial longitudinal register with the axis 203 of bar-element articulation. In this way, it is assured that the straight proximal end of bar element 202 and the straight proximal end of the a intramedullary nail are parallel at their respective connections to handle 209; and at the same time, the straight distal end of bar element 201 and the straight distal end of the intramedullary nail are also parallel, when drill guides 131, 131' align with the distal bolt holes of nail 210.

Near its distal end, the distal bar element 201 is seen to include a vertically open elongate slot 211, of width to permit passage of drill guides 131, 131' therethrough and to allow an adjustable range of longitudinally guided displacement of slide 200 and the drill guides carried thereby. As shown, a longitudinal slot 214 in a side wall of slide 200 will be understood to provide access for a short threaded bolt or shank to engage a local threaded hole in the adjacent side wall of the distal-bar element 201, and a manipulating knob 215 for the threaded bolt provides selectively operable means for clamping an adjusted longitudinal position of slide 200 (and its drill guides), within a longitudinal range that is determined by the length of slot 212. The threaded hole engaged by the threaded shank of knob 215 may be one of a longitudinally spaced plurality of the same, thus enabling slide 200 to be adjustably clamped to bar member 201 over a continuous range which approaches the length of the bar slot 211.

Slide 200 is shown to be carrying outrigger structure 216, secured to slide 200 (by bolt means that is suggested at 217. The outrigger structure extends distally downward to provide guided support for a contact rod 218 to contact the intramedullary nail, near the distal end of the nail, with the axis of rod 218 aligned for intersection with the axis of the nail and perpendicular to a geometric plane which includes the axes of drill guides 131, 131' as well as the axis of the nail near its distal end. Collars 235, 236 will be understood to be releasably clamped to contact rod 218; in the manner described for other embodiments, to preserve a calibrated projecting length to the point of rod-to-nail contact. And drill guides 131, 131' may be adjustably retained in spaced vertical bores of slide 200, as by setscrews 221, 221'.

Finally, the described jig of FIG. 12 will be understood to be fully reversible with respect to the direction of lateral offset shown. The reversibility is accomplished by loosening setscrews 221, 221' to permit removal of the drill guides from bar-member slot 211, and by removing knob 213 and its shank from engagement with the near side wall of bar element 201, at which point slide 200 (and its outrigger) is free to slide off the distal end of bar element 201. Upon end-for-end reversal of slide 200 with its outrigger 215, the end-for-end reversed slide 200 may be reassembled to the distal end of bar element 201, and outrigger 215 will have been positioned with its lateral offset on the near side of bar element 201 (in the sense of the drawing, FIG. 12), and with slide 200 secured by bolt 213 passing through a corresponding slot (212) in the opposite side wall of slide 200 and in threaded engagement with a tapped hole in the opposite side wall of bar element 201.

Operational use of the jig structure of FIG. 12 will be seen to be very much as described for other embodiments. As a first step prior to nail installation in a patient, and with the intramedullary nail 210 chucked to handle 209, the proximal bar element 202 should be longitudinally positioned and clamped at 214 to handle 209 so that the articulation axis 203 is in substantial register with the longitudinal center of the bend of nail 210. Then, the angle of articulation between bar elements 201, 202 should be adjusted to assure a parallel relation between bar element 201 and the distal region of the nail that includes the bolt holes with which bone drilling is later to be accomplished. With its clamp knob in loose condition, slide 200 may be displaced along bar element 201 until a plug gage, guided by one of the drill guides is also able to enter its bolt or bone-screw hole in the distal end portion of nail 210. Preferably, a second plug gage is used to establish alignment of the other drill guide with the second bolt hole, and a trimming adjustment at knob 204 may be made to assure the desired parallel relation between the nail axis (in the distal region of the two bolt holes) and the axis of the distal-bar element 201; the use of two plug gages in this way will assure that a nail-contacting position established for rod 218, and maintained by setscrew fastening of collar 235 to rod 218 when the collar is abutted to outrigger 216, will faithfully serve to re-establish the correctly guided drilling of bone on the transverse alignment of one of the distal bolt holes of the nail.

What is claimed is:

1. The method of presetting a drill jig for aligning at least one drill guide with a transverse bone-screw hole in an intramedullary nail that is to be installed in a fractured bone, wherein the intramedullary nail has (i) a proximal-end portion for selective jig attachment and (ii) a straight elongate distally extending portion having said bone-screw hole, and wherein said jig comprises (a) an elongate bar and (b) a bar-positioning handle having means for keyed selective connection to the nail such that said handle extends transversely of the nail and positions said bar parallel to said distally extending portion, (c) a distal formation carried by said bar and having first and second guide bores, one of said guide bores being aligned perpendicular to and defining with the nail a first geometric plane which is to include the bone-screw hole, and the other of said guide bores being aligned perpendicular to and defining with the straight distal portion of the nail a second geometric plane which is perpendicular to said first geometric plane; said method comprising the steps of:

(1) assembling the drill jig to the intramedullary nail prior to nail installation in the fractured bone, and with said one drill guide in one of said guide bores;

(2) selecting and adjustably positioning a nail-contact rod in the other of said guide bores such that said rod may be positioned in contact with the nail;

(3) aligning said one drill guide of the jig with the bone-screw hole of the intramedullary nail;

(4) adjustably positioning the nail-contact rod into contact with the nail in the circumstance of achieving the alignment of step (3), thereby establishing a nail-calibrated reference position of the contact rod, and marking the nail-calibrated position of the contact rod with reference to a part of said jig so that the nail-contact rod may be removed without loss of the marked nail-calibrated reference position; and (5) disassembling the nail-contact rod from the jig so that the nail can be inserted in the fractured bone before local surgery to permit reassembly of the nail-contact rod to the nail and re-established assembly of the nail-contact rod to the jig pursuant to said nail-calibrated reference and in contact with the nail.

2. The method of claim 1, wherein the distal formation carried by said bar comprises a slide member having longitudinal guidance on the bar, and in which the aligning of step (3) includes such longitudinal displacement of said slide member as is necessary to position a plug gage in mechanical connection of said one drill guide of the jig in alignment with the bone-screw hole of the intramedullary nail.

3. The method of claim 1, wherein the intramedullary nail has a bend between said straight distal portion and a straight proximal end portion for selective jig attachment and in which said elongate bar comprises hinge-connected proximal and distal elements with the proximal element parallel to the straight proximal end portion of the intramedullary nail, wherein step (1) additionally includes the manipulation of said distal element into parallel relation with the straight distal portion of said intramedullary nail.

4. The method of presetting a drill jig for aligning two spaced parallel drill guides with two spaced parallel transverse bone-screw holes in an intramedullary nail that is to be installed in a fractured bone, wherein the intramedullary nail has a bend between a straight distal-end portion having said bone-screw holes and a straight proximal-end portion; and wherein said jig comprises (a) an elongate bar having an adjustably clamped articulating-hinge connection between straight proximally extending and distally extending portions of said bar and (b) a bar-positioning handle having means for keyed selective connection to the nail such that said handle extends transversely of the nail, said handle having releasably clamped longitudinally positioning connection to the proximally extending portion of the bar such that said distally extending portion may be articulated into parallel relation with the straight distally extending portion of the nail when the nail is in keyed connection to said handle, and (c) a distal formation carried by the distally extending portion of said bar and having first and second guide-bore means, one of said guide-bore means comprising two spaced parallel guide bores having axes adapted for drill guidance when in alignment with the respective axes of the bone-screw holes, the axes of said spaced parallel guide bores establishing a geometric plane, the other of said guide-bore means having an axis perpendicular to the straight distally extending portion of the nail and to said geometric plane; said method comprising the steps of:

(1) assembling the drill jig to the intramedullary nail prior to nail installation in the fractured bone, with said clamping means released to permit longitudinal displacement of said bar with respect to said handle, and with said one drill guide in one of said guide bores;

(2) selecting and adjustably positioning a nail-contact rod in the other of said guide-bore means such that said rod may be positioned in contact with the nail;

(3) aligning said two spaced parallel guide bores of the jig with the respective bone-screw holes of the intramedullary nail, thereby establishing said geometric plane;

(4) adjustably positioning the nail-contact rod into contact with the nail in the circumstance of achieving the alignment of step (3), thereby establishing a nail-calibrated reference position of the contact rod, and marking the nail-calibrated position of the contact rod with reference to a part of said jig so that the nail-contact rod may be removed without loss of the marked nail-calibrated reference position; and (5) disassembling the nail-contact rod from the jig so that the nail can be inserted in the fractured bone before local surgery to permit reassembly of the nail-contact rod to the nail and re-established assembly of the nail-contact rod to the jig pursuant to said nail-calibrated reference and in contact with the nail.

5. The method of claim 4, in which step (3) comprises selecting two plug gages and positioning a separate one and a separate other of said plug gages in mechanical connection of the respective drill guides of the jig in mechanical alignment with the respective bone-screw holes of the intramedullary nail.

6. The method of presetting a drill jig for aligning at least one drill guide with a transverse bone-screw hole in an intramedullary nail that is to be installed in a fractured bone, wherein the intramedullary nail has (i) a proximal-end portion for selective jig attachment, (ii) a straight distally extending portion having said bone screw hole, and (iii) a bend portion between said proximal-end and distally extending portions, said portions of the nail being essentially contained in a single geometric plane, with the axis of the bone-screw hole oriented normal to said single geometric plane; and wherein said jig comprises (a) an elongate bar having a releasably clamped articulating hinge connection between proximally extending and distally extending portions of said bar and (b) a bar-positioning handle having means for keyed selective connection to the nail such that said handle extends transversely of the nail, said handle having releasably clamped longitudinally positioning connection to the proximally extending portion of the bar such that said distally extending portion may be articulated into parallel relation with the straight distally extending portion of the nail when in keyed connection to said handle, and (c) a distal formation carried by the distally extending portion of said bar and having first and second guide bores, one of said guide bores having an axis adapted for drill guidance when in alignment with the axis of the bone-screw hole, and the axis of the other of said guide bores being aligned in said geometric plane and being adapted for alignment with the bone-screw hole of the key-connected nail; said method comprising the steps of:

(1) assembling the drill jig to the intramedullary nail prior to nail installation in the fractured bone, with said one drill guide in said one guide bore;

(2) selecting and positioning a plug gage for mechanical connection of said one drill guide with the bone-screw hole of the intramedullary nail, and to the extent necessary, releasing one or both of said releasably clamped connections for hinge-articulation adjustment and/or for longitudinal adjustment of the bar connection to said handle, before reclamping these adjustments upon achievement of plug-gage alignment of the drill guide with the bone-screw hole;

(3) selecting and positioning a nail-contact rod in the other of said guide bores such that said rod is in contact with the nail, thus establishing a nail-calibrated position of the contact rod with reference to a part of said jig;

(4) establishing a marked reference for said nail-calibrated position of the contact rod with reference to a part of said jig, said marked reference being such that upon disassembly of said jig to permit nail installation in the fractured bone, the nail-contact rod can be removed without loss of said marked reference; and (5) disassembling the jig and plug gage from the nail and removing the nail-contact rod from the jig so that the nail can be inserted in the fractured bone before local surgery to permit reassembly of the jig to the nail and reestablished mounting of the nail-contacting rod to the jig pursuant to said reference and in contact with the nail.

* * * * *

UNITED STATES PATENT AND TRADEMARK OFFICE
CERTIFICATE OF CORRECTION

PATENT NO. : 5,766,179
DATED : June 16, 1998
INVENTOR(S) : Giovanni FACCIOLI and Stefano ROSSI It is certified that error appears in the above-indentified patent and that said Letters Patent is hereby corrected as shown below:

Column 4, lines 5 to 6;   after "acute angle" delete "a" and insert therefor --$\alpha$--

Column 12, line 60;   after "of the" delete "a" before "intramedullary nail"

Signed and Sealed this

First Day of September, 1998

BRUCE LEHMAN

Attest:

Attesting Officer

Commissioner of Patents and Trademarks